(12) United States Patent
Sigmon, Jr. et al.

(10) Patent No.: US 10,045,870 B2
(45) Date of Patent: Aug. 14, 2018

(54) SUPPORT DEVICE FOR GASTROINTESTINAL IMPLANT

(71) Applicant: Cook Medical Technologies LLC, Bloomington, IN (US)

(72) Inventors: John Crowder Sigmon, Jr., Winston-Salem, NC (US); Gregory James Hardy, Winston-Salem, NC (US); Shaun D. Gittard, Wiston-Salem, NC (US); Tyler Evans McLawhorn, Winston-Salem, NC (US); Michelle D. Martinez, Winston-Salem, NC (US); Vihar C. Surti, Winston-Salem, NC (US)

(73) Assignee: Cook Medical Technologies LLC, Bloomington, IN (US)

(*) Notice: Subject to any disclaimer, the term of this patent is extended or adjusted under 35 U.S.C. 154(b) by 198 days.

(21) Appl. No.: 15/226,631

(22) Filed: Aug. 2, 2016

(65) Prior Publication Data
US 2017/0035594 A1 Feb. 9, 2017

Related U.S. Application Data

(60) Provisional application No. 62/201,897, filed on Aug. 6, 2015.

(51) Int. Cl.
*A61M 5/00* (2006.01)
*A61F 5/00* (2006.01)
(Continued)

(52) U.S. Cl.
CPC .............. *A61F 5/0069* (2013.01); *A61F 2/04* (2013.01); *A61F 5/0036* (2013.01);
(Continued)

(58) Field of Classification Search
CPC ........ A61F 5/02; A61F 5/0069; A61F 5/0076; A61F 5/0079; A61F 5/0083;
(Continued)

(56) References Cited

U.S. PATENT DOCUMENTS 9,011,365 B2 * 4/2015 Connor ................. A61F 5/0076
600/37
9,044,300 B2 * 6/2015 Belhe .................... A61F 5/0076
(Continued)

FOREIGN PATENT DOCUMENTS

WO WO 2006/102240 A2 9/2006
WO WO 2011/085234 A1 7/2011

OTHER PUBLICATIONS

Communication—Extended Search Report dated Jan. 2, 2017 for EP Application No. 16183138.3 (6 pp.).

*Primary Examiner* — Philip R Wiest
(74) *Attorney, Agent, or Firm* — Brinks Gilson & Lione

(57) ABSTRACT

The present disclosure provides a support device for a gastrointestinal implant. The support device may include a lumen configured to extend through a submucosal tunnel and a mouth located at a proximal end of the lumen and in fluid communication with the lumen. The mouth may be configured to face proximally within a gastrointestinal tract to receive GI contents, and the mouth may be configured to direct the GI contents into the lumen. The support device may further include a support structure, where the lumen extends through the support structure, and where the support structure is configured to apply an outward radial force on an inner wall of the gastrointestinal tract. An artificial tunnel may extend distally from the support structure, may form at least a portion of the lumen, and may be configured to extend through the submucosal tunnel.

20 Claims, 12 Drawing Sheets

(51) Int. Cl.
*A61F 2/04* (2013.01)
*A61M 27/00* (2006.01)

(52) U.S. Cl.
CPC ......... *A61F 5/0076* (2013.01); *A61M 27/002* (2013.01); *A61F 2002/045* (2013.01)

(58) Field of Classification Search
CPC .... A61F 5/0086; A61F 5/0089; A61F 5/0036; A61F 2002/045; A61M 27/002
See application file for complete search history.

(56) References Cited

U.S. PATENT DOCUMENTS

2011/0087146 A1\* 4/2011 Ryan ..................... A61F 2/04
604/8
2011/0208158 A1\* 8/2011 Sigmon, Jr. ........ A61B 17/3478
604/506

\* cited by examiner

SUPPORT DEVICE FOR GASTROINTESTINAL IMPLANT

RELATED APPLICATIONS

The present patent document claims the benefit of the filing date under 35 U.S.C. § 119(e) of Provisional U.S. Patent Application Ser. No. 62/201,897, entitled "SUBMUCOSAL TUNNEL FOR OBESITY," filed Aug. 6, 2015, which is hereby incorporated by reference in its entirety.

BACKGROUND

Gastric bypass surgery is a medical procedure to reduce the functional size of the stomach of a patient. The result of the procedure is an altered response to the intake of food or other ingested substances. The procedure is often used to treat patients suffering from obesity and other medical conditions tied to food intake.

One popular form of the procedure is Roux-en-Y gastric bypass. In a Roux-en-Y procedure, the surgeon creates a small stomach pouch and then creates a bypass to the small intestines with an alimentary limb. As a result, food bypasses the majority of the stomach when traveling through the gastrointestinal tract. The smaller functional area of the stomach limits the amount of food a patient can comfortably eat, thereby decreasing the overall intake of calories.

Sleeve gastrostomy is another popular surgical weight-loss procedure. In this procedure the stomach is reduced to a fraction of its original size by stapling and removing a portion of the stomach along its greater curvature. This procedure is increasing in popularity, as it is an easier procedure with fewer complications as compared to a Roux-en-Y procedure, and it has comparable results in terms of weight loss.

Another procedure that restricts food intake is the Magenstrasse and Mill Procedure. In this procedure, a narrow gastric tube is created by stapling from the antrum up to the fundus, thereby reducing the functional size of the stomach to restrict food intake. Although the fundus and greater curve of the stomach remain in situ, the functional portion of the stomach is limited to the lesser curvature formed by the stapling.

While the described procedures have been effective in facilitating weight loss, they are associated with several disadvantages. Each of the described procedures is highly invasive and requires extensive modifications of the natural internal anatomy of a patient. They each come with complications often associated with highly invasive surgery, including bleeding, anesthesia complications, deep vein thrombosis, staple line leaking, infection, etc. The threat of these complications may limit the number of obese patients or patients with other disorders who are able to benefit from gastric bypass procedures, as these patients are often particularly sensitive to medical complications.

BRIEF DESCRIPTION

In one aspect, the present disclosure provides a support device for a gastrointestinal implant. The support device may include a lumen configured to extend through a submucosal tunnel. A mouth may be located at a distal end of the lumen and may be in fluid communication with the lumen. The mouth may be configured to face proximally within a gastrointestinal tract receive GI contents, and the mouth may be configured to direct the GI contents into the lumen. The support device may also include a support structure, where the lumen extends through the support structure. The support structure may be configured to apply an outward radial force on an inner wall of the gastrointestinal tract.

The support structure may include a first portion and a second portion located distally of the first portion. A diameter of the first portion may be larger than a diameter of the second portion.

The first portion may be configured to be located within a native lumen of the gastrointestinal tract. The second portion may be configured to be located in a submucosal tunnel.

The support device may include an artificial tunnel extending distally from the support structure, where the artificial tunnel forms at least a portion of the lumen, and where the artificial tunnel is configured to extend through the submucosal tunnel.

The artificial tunnel may be semi-permeable.

The artificial tunnel may include an outer surface with a surface characteristic configured to facilitate tissue ingrowth.

The artificial tunnel may be configured to extend to a distal end of the submucosal tunnel. The artificial tunnel may include a distal mouth configured to discharge GI contents into a native portion of the gastrointestinal tract.

The support structure may include a stent.

The support device may have a feeding tube having the lumen and the mouth. A balloon may include the support structure. The feeding tube may extend substantially through the balloon.

In another aspect, the present disclosure may provide a gastrointestinal implant. The gastrointestinal implant may include a support device with a first portion configured for installation in a native lumen of a gastrointestinal tract and a second portion configured for installation in a submucosal tunnel. The first portion of the support device may have a first diameter at least as large as a diameter of the native lumen, and the second portion may have a diameter substantially the same size as a diameter of the submucosal tunnel or smaller than the diameter of the submucosal tunnel.

The gastrointestinal implant may include a mouth at a proximal end of the support device and a lumen extending through the support device and in fluid communication with the mouth.

The first portion of the support device may include a stent.

An artificial tunnel may extend distally from the support device and through the submucosal tunnel.

The artificial tunnel may be semi-permeable.

The artificial tunnel may be configured to extend to a distal end of the submucosal tunnel. The artificial tunnel may also include a distal mouth configured to discharge GI contents into a native portion of the gastrointestinal tract.

In another aspect, the present disclosure may provide a method. The method may include displacing a flap of submucosal tissue from a submucosal layer within a native lumen of a gastrointestinal tract. The method may also include adhering the flap to an opposite-side wall of the native lumen.

The method may include inverting an end of the submucosal flap and placing the inverted end of the flap in contact with the opposite side wall.

The method may include creating an injury site on the opposite side wall by removing mucosal tissue, where the inverted end of the flap is placed in contact with the injury site.

The method may include applying a pressure to the flap with a support device while the flap is in contact with the opposite-side wall with a support device.

The method may include removing the first support device and deploying a second support device. The second support device may be configured to redirect GI contents from the native lumen of the gastrointestinal tract to a submucosal tunnel.

In another aspect, the present disclosure may provide a method for forming a bypass tunnel, the method including separating a portion of a submucosal layer from a wall of an esophagus to form a tunnel, extending the tunnel beneath or within the submucosal layer to a location within the wall of a stomach, and forming an incision in the distal end of the tunnel to form an exit within the stomach.

The method may further include forming an incision in the proximal end of the tunnel. In some embodiments, a fluid is injected into or beneath the submucosal layer to separate the submucosal layer from the wall of the esophagus. The fluid may be injected into or beneath the submucosal layer to extend the tunnel to a location within the wall of the stomach.

A plurality of entrance locations for the injection of the fluid may be used. A tunneling device with a cutting end may be used to separate the portion of the submucosal layer from the wall of the esophagus. A support device, which may be expandable, may be deployed in the tunnel.

DETAILED DESCRIPTION

Figure 1:
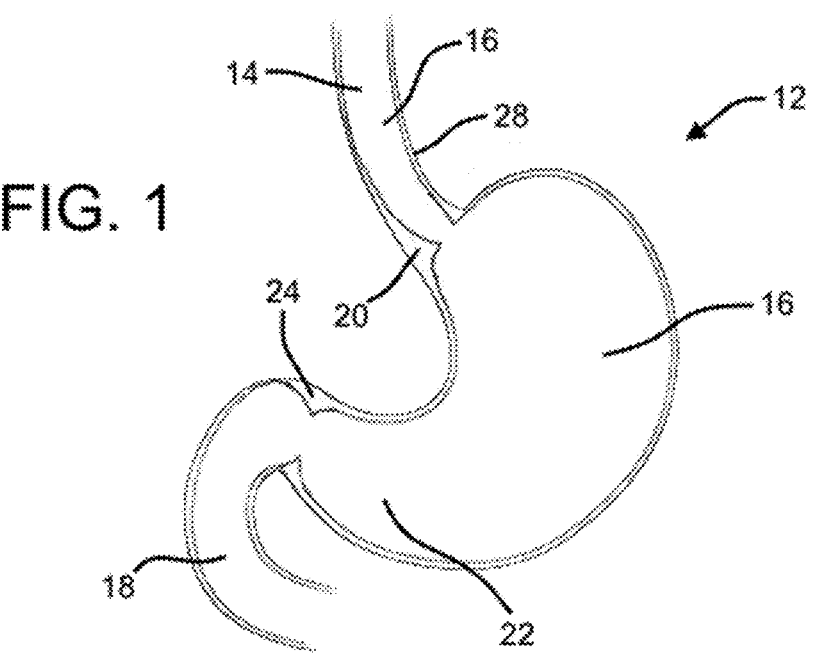
FIG. 1 is a sectional view of a portion of the gastrointestinal tract of a patient.

The invention is described with reference to the drawings in which like elements are referred to by like numerals. The relationship and functioning of the various elements of this invention are better understood by the following detailed description. However, the embodiments of this invention are not limited to the embodiments illustrated in the drawings. It should be understood that the drawings are not to scale, and in certain instances details have been omitted which are not necessary for an understanding of the present invention, such as conventional fabrication and assembly.

As used in the specification, the terms "proximal" and "distal" should be understood as being in the terms of the direction of flow of the gastrointestinal tract. Hence the term "distal" means downstream (e.g., generally lower) within the gastrointestinal tract, and the term "proximal" means the upstream (e.g., generally higher) within the gastrointestinal tract.

FIG. 1 is an illustration of the gastrointestinal tract of a human patient prior to the deployment of a gastric bypass device. Referring to FIG. 1, the gastrointestinal tract 12 of a patient normally comprises an esophagus 14, a stomach 16, and a duodenum 18. Consumed food or other ingested substances move in the distal direction down the esophagus 14, through a lower esophageal sphincter 20, and into the stomach 16. The stomach 16 comprises a pyloric antrum 22 near the distal end of the stomach 16, which then leads through a pyloric sphincter 24 and into duodenum 18.

Figure 2:
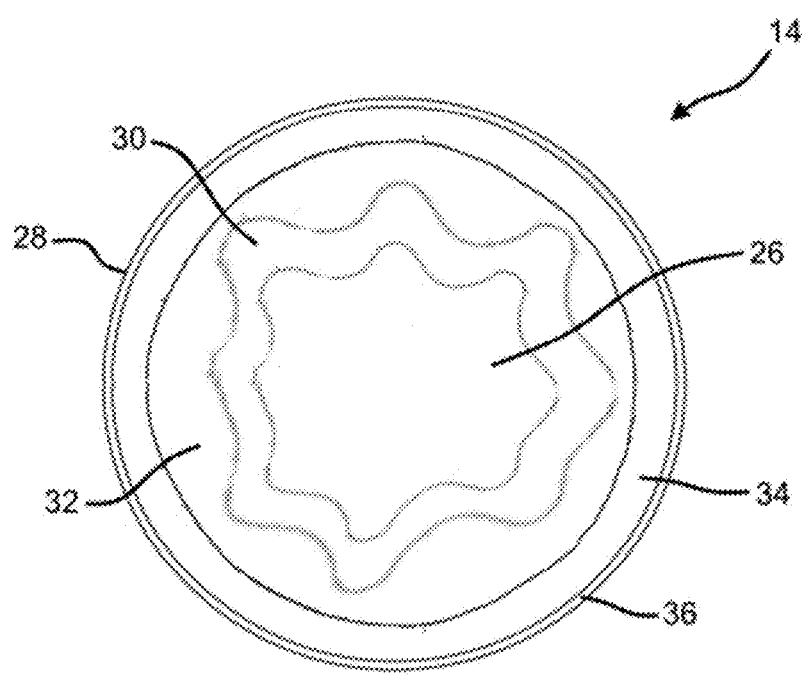
FIG. 2 is a top cutout view of an esophagus depicting the natural tissue layers of the gastrointestinal tract.

As illustrated in FIG. 2, the outer walls of gastrointestinal tract generally comprise several tissue layers. For example, in the esophagus 14, starting from a native lumen 26 of the esophagus 14 and moving in a radially-outward direction, a wall 28 comprises a mucous membrane (e.g., the mucosa 30), a submucosal layer of dense connective tissue for supporting the mucosa (shown as the submucosal layer 32), a layer of smooth muscle (the muscularis propria 34), and a layer of serous membrane (the serosa 36). Other portions of the wall 28 outlining other areas of the gastrointestinal tract, such as the stomach 16 and the duodenum 18 (shown in FIG. 1), may comprise a similar anatomy.

Figure 3:
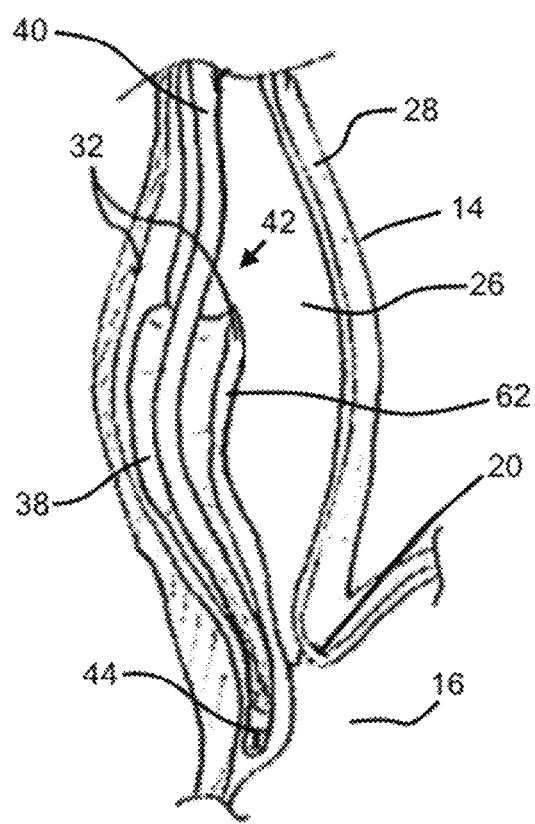
FIG. 3 is a sectional view of a submucosal tunnel formed near the distal end of the esophagus in accordance with the present disclosure.

Referring to FIG. 3, a submucosal tunnel 38 may be formed beneath or within the submucosal layer 32. It will be appreciated, however, that the disclosed embodiments herein are not limited with respect to only a submucosal layer and underling mucosa, but may be applied to any two adjacent layers of suitable human or animal tissue. The submucosal tunnel 38 may be provided to bypass at least a portion of the esophagus 14 and/or the stomach 16. As depicted, the submucosal tunnel 38 may be formed in the esophagus 14 within the submucosal layer 32 or between the submucosal layer 32 and an underlying layer (such as the muscularis propria 34, shown in FIG. 2). In some embodiments, the submucosal tunnel 38 may extend into, and potentially distally beyond, the stomach 16.

Providing the submucosal tunnel 38 may provide the benefits of other gastric bypass procedures by, for example, bypassing a proximal portion of the stomach 16 and directing GI contents from the esophagus 14, through the submucosal tunnel 38, directly to a distal portion of the stomach 16 adjacent to the antrum 22. Herein, gastrointestinal contents, or "GI contents," refer to solids and fluids (e.g., food and other ingested solids, water and other ingested fluids, body fluids, gasses, and the like) that travel through the gastrointestinal tract, typically moving in the distal direction. Advantageously, bypassing at least a portion of the stomach 16 may reduce the functional size of the gastrointestinal tract to limit the amount of food a patient may comfortably ingest. Further, the described procedure for forming the submucosal tunnel 38 may be significantly less invasive than known gastric bypass procedures because the devices described herein for forming a submucosal tunnel 38 may, for example, enter from the proximal direction of the esophagus (e.g., through the mouth) without creating large surgical openings in the body. Further, the anatomy of a patient may remain significantly in-tact and undamaged with respect to other gastric bypass procedures, which may limit the threat of significant complications that arise from other procedures that require invasive surgery and heavy modifications to anatomy of the gastrointestinal tract. The submucosal tunnel 38 may be maintained with a gastrointestinal implant having an artificial tunnel 314 with a distal mouth 232, which is described in detail below.

The submucosal tunnel 38 may be formed by operating a tunneling device 40 during a tunneling procedure. For example, to form the submucosal tunnel 38, a peroral endoscopic myotomy (or "POEM") procedure may be utilized. In this procedure, a small incision is made into the mucosa and/or the submucosal layer 32 to create an opening 42 in the esophagus 14, which may be entered by the tunneling device 40. The tunneling device 40 may comprise a cutting end 44 or another suitable mechanism for cutting or otherwise separating at least a portion of the submucosal layer 32 from adjacent material. The tunneling device 40 may continue distally to form the submucosal tunnel 38 such that it extends past the esophageal sphincter 20 and into a portion of the submucosal layer 32 within the outer wall of the stomach 16. The submucosal tunnel 38 may extend to, for example, the antrum 22 (as shown), the duodenum 18, or in another location.

In some embodiments, the tunneling device 40 may continue to tunnel in the distal direction to a predetermined location along the lesser curvature of the stomach 16. After completing the tunneling procedure, an incision may be made adjacent to the distal end of the submucosal tunnel 38 to provide a distal opening, depicted as the opening 43, which may serve as an outlet to discharge GI contents. While it may be preferable to provide the submucosal tunnel 38 along the lesser curvature, the submucosal tunnel 38 may alternatively be provided along the greater curvature or at any other location along the anatomy of the stomach 16.

Figure 4:
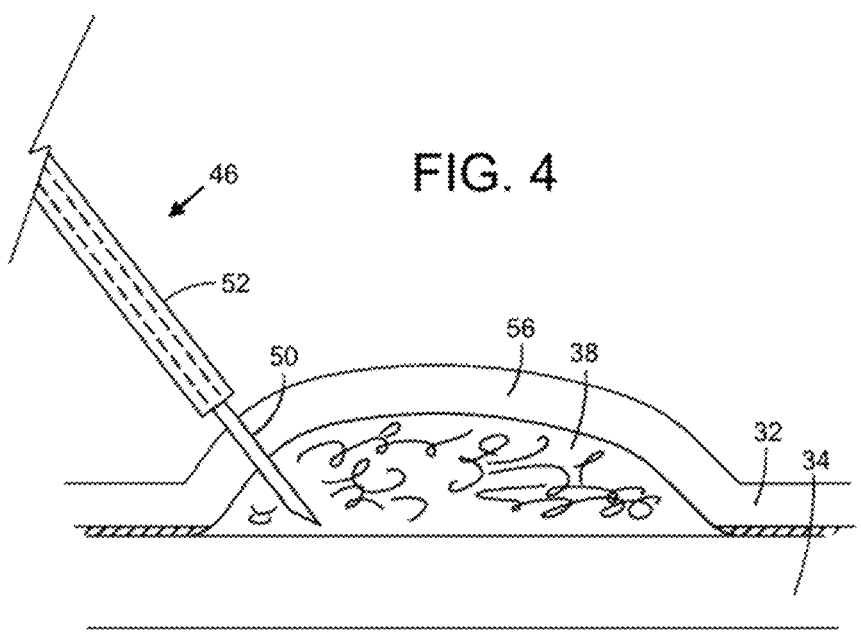
FIG. 4 is a partial side view of a distal end of an embodiment of a delivery device at a tissue treatment site.

Referring to FIG. 4, in some embodiments, a submucosal tunnel 38 may be formed by injecting an injectable solution or other fluid, such as a thick, viscous gel, beneath (or within) the submucosal layer 32 to separate the submucosal layer 32 from the adjacent layer of tissue. One procedure for injecting a solution described in U.S. Patent Application Publication No. 2011/0208158 to Sigmon et al., which is herein incorporated by reference in its entirety. The injectable solution or gel is preferably a pharmaceutically acceptable solution for use in humans and animals that has minimal tissue reactivity. In some embodiments, the injectable solution has a viscosity greater than about 10,000 cP, and in some embodiments, a viscosity greater than about 30,000 cP and greater than about 50,000 cP. The preferred viscosity for the injectable solution is between about 10,000 to 150,000 cP, and in some embodiments the preferred viscosity for the injectable solution is between about 30,000 cP and about 120,0000 cP, although other viscosities may be used. The viscosity of the injectable solution preferably should be high enough to separate the tissue layers. Non-limiting examples of suitable materials for inclusion in the injectable solution include methylcelluloses, such as carboxymethyl cellulose (CMC) and hydroxypropyl methylcellulose (HPMC), extracellular matrix proteins, elastin, collagen, gelatin, fibrin, agarose, and alginate or mixtures thereof. The injectable solution will be described with reference to CMC although one skilled in the art will understand other suitable materials may also be used to form the injectable solution.

Suitable concentrations of the CMC for the injectable solution include about 1% to 10% CMC (e.g. about 1%, 1.5, 2%, 2.5%, 3%, 3.5%, 4%, 4.5%, 5%, 5.5%, 6%, 6.5%, 7%, 7.5%, 8%, 8.5%, 9%, 9.5%, or 10%). Preferably CMC concentrations range from about 2.5% to 3.5%, and more preferably about 3%. The CMC may be mixed with sterile water, saline or other pharmaceutically acceptable solution to provide a suitable concentration for injection (CMC may be purchased from Sigma Aldrich, St. Louis, Mo.). The injectable solution may also include additional components, including, but not limited to dyes, such as food coloring, methylene blue or carbon black, and hemostasis regulators, such as vasoconstrictors, for example, epinephrine. In operation, the CMC is premixed with a pharmaceutically acceptable solution at the manufacturer to the desired concentration for the injectable solution.

FIG. 4 illustrates a delivery device 46 for delivering an injectable solution to a tissue treatment site. A distal portion 48 of the delivery device 46 is shown with an inner shaft 50 extending out of an outer catheter 52 so that the inner shaft 50 extends into the tissue, which may tissue defining the wall of the gastrointestinal tract. The inner shaft 50 may be a needle, a cannula, or other elongate tubular structure suitable for insertion into tissue. The inner shaft 50 may be inserted adjacent layers of tissue, for example, the muscularis propria 34 and the submucosal layer 32. The injectable solution may form a fluid-filled pocket, and the pressure of the solution may force separation between the muscularis propria 34 and the submucosal layer 32, breaking the attachments between the tissue layers.

Figure 5:
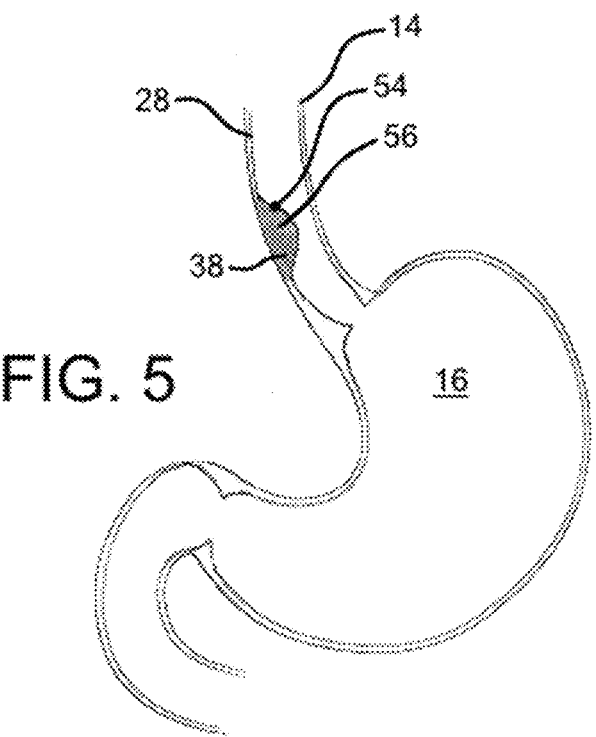
FIG. 5 is a sectional view of a portion of the gastrointestinal tract of a patient depicting a fluid-filled pocket within the submucosal layer in the esophagus in accordance with the present disclosure.
Figure 6:
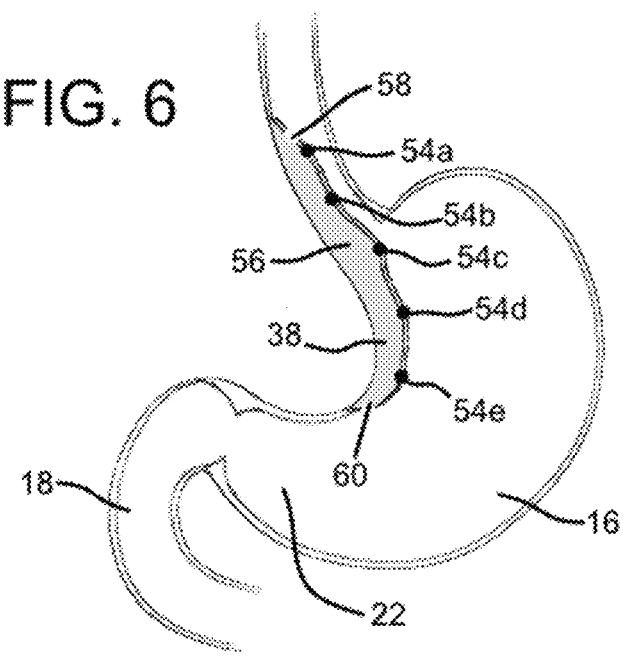
FIG. 6 is a sectional view of a portion of the gastrointestinal tract of a patient with a fluid-filled pocket formed in or under the submucosal layer along the esophagus and lesser curvature of the stomach in accordance with the present disclosure.

Referring to FIG. 5, injection may occur at an entry location 54 to form a fluid-filled pocket 56. As the solution is injected, the pocket 56 may increase in size, causing the pocket 56 to expand along the wall 28. The direction of expansion of the pocket 56 may be controlled in any suitable matter, for example by applying a pressure to certain areas of the inner surface of the wall 28 during injection or by precisely controlling the pressure and direction of the injected solution from a delivery device. As depicted by FIG. 6, the pocket 56 may be expanded proximally and/or distally to extend from the esophagus 14 to a location along the lesser curvature of the stomach 16. In other embodiments, the pocket 56 may extend along a different portion of the stomach 16, for example along the greater curvature. The pocket 56 may define the submucosal tunnel 38.

While it is contemplated to have only a single entry location for fluid injection, it may be advantageous to have multiple entry locations for fluid injection to accurately and precisely place the submucosal tunnel 38, particularly since the direction of expansion of a pocket from a single entry location may not be easily controllable may cause a corresponding pocket to expand unpredictably. Referring to FIG. 6, a multiple entry locations 54a-e are depicted. A plurality of separate and potentially isolated pockets (not shown) may be formed at each of the plurality of entry locations 54a-e. These pockets may be filled and eventually expand into one another to form one relatively large fluid-filled pocket 56 corresponding with the desired track of the submucosal tunnel 38. In some embodiments, a cutting device (e.g., the tunneling device 40 of FIG. 3) may be used to connect the plurality of pockets. Alternatively, a delivery device 46 (see FIG. 4) may inject at a single entry location until the desired expansion of the pocket 56 is complete or becomes difficult to control. If further expansion is desired, a medical professional may maneuver the delivery device 46 to a second entry location (e.g., distally of the first entry location), and then inject more solution into the existing pocket at that second entry location to cause further expansion. This procedure may be repeated as necessary.

After the pocket 56 is formed, an incision may be made at the proximal end of the pocket 56, for example to form a proximal opening 58 of the submucosal tunnel 38. The proximal opening 58 may be made with an endoscope or another suitable device. The endoscope or other suitable device may then advance through the formed submucosal tunnel 38 to then form an incision defining a distal opening 60 of the submucosal tunnel 38. The distal opening 60 may be adjacent to the stomach 16, and may be adjacent to antrum 22 as shown in FIG. 6. In other embodiments, the distal opening 60 may be located at another location, such as adjacent to the duodenum 18. In some cases, the injected solution or other fluid will naturally or automatically leak out of the distal opening 60, though this is not necessary. It is contemplated that, once the submucosal tunnel 38 is formed, the solution may be suctioned or otherwise flushed out of the submucosal tunnel 38, may be forced out during the deployment of a structure within the submucosal tunnel 38, or may remain within the submucosal tunnel 38.

Figure 7:
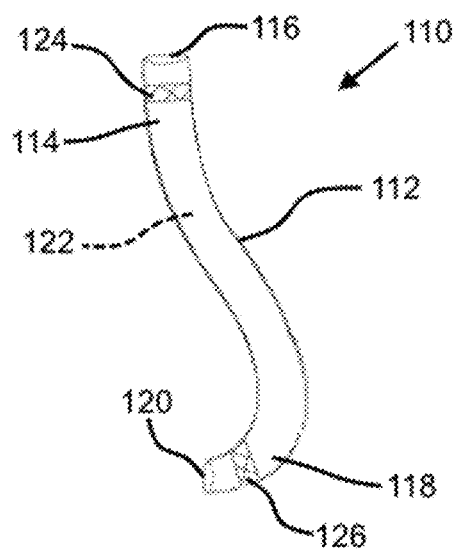
FIG. 7 is a perspective view of a support device with a stent at the distal and proximal ends in accordance with the present disclosure.

Referring to FIG. 7, after formation of the submucosal tunnel, it may be preferable to deploy a gastrointestinal implant, such as the depicted reinforcing structure or support device 110, within the submucosal tunnel 38 (see FIG. 8) to prevent the submucosal tunnel 38 from collapsing and to facilitate the passage of GI contents through the tunnel. For example, referring to FIG. 7, the support device 110 may include a tubular body or other artificial tunnel 112 with a proximal end 114 having a proximal opening 116 and a distal end 118 having a distal opening 120. The artificial tunnel 112 may be formed, for example, by an expandable stent (covered or uncovered), a flexible hose, or any other suitable structure. A lumen 122 may extend from the proximal opening 116 to the distal opening 120, and may be configured for the passage of GI contents therethrough. In some embodiments, one or more stents 124, 126 may be provided at the proximal end 114 and/or the distal end 118. While not depicted here, it is contemplated that the support device 110 may be formed entirely of a stent.

Figure 8:
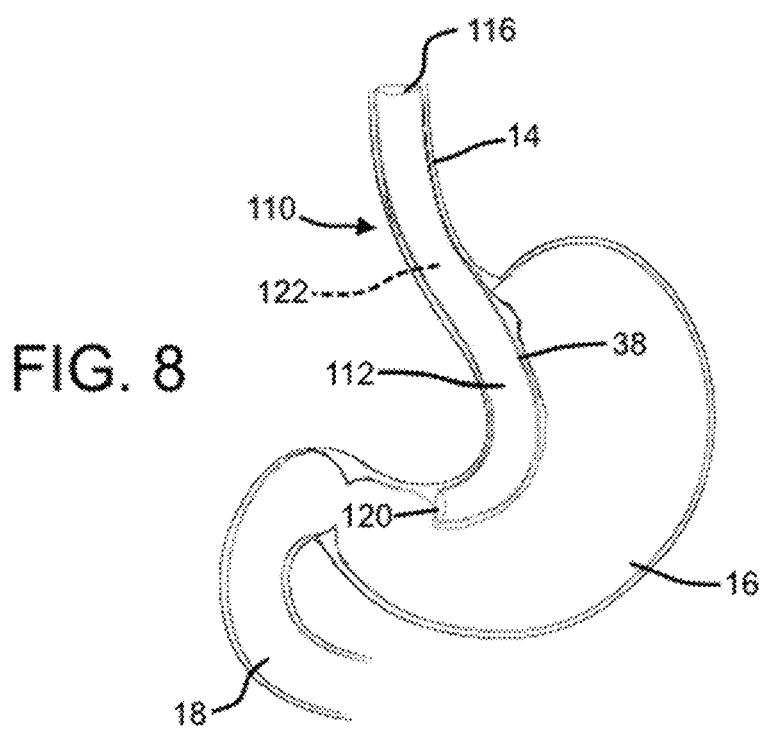
FIG. 8 is a sectional view of a portion of the gastrointestinal tract of a patient with a support device deployed within a submucosal tunnel in accordance with the present disclosure.

As shown in FIG. 8, the mouth or proximal opening 116 may be located in the esophagus 14 and may face proximally when deployed. The distal opening 120 may be located within the stomach 16, for example, adjacent to the antrum 22 as shown. In other embodiments, the distal opening 120 may be located in other areas of the stomach 16, in the duodenum 18, or in another location. In some embodiments the artificial tunnel 112 may be flexible to allow the natural body response of contracting with unidirectional waves to alter the shape of the support device 110, thereby forcing food in the distal direction. In other words, the artificial tunnel 112 may be capable of flexing to move with the peristaltic motion of the gastrointestinal tract to allow GI contents to be moved through the artificial tunnel 112. While not required, the artificial tunnel 112 may create a fluid barrier between the lumen 122 and the surrounding body tissue layers (such as the submucosal layer).

One method of placing the support device 110 may include placement via fluoroscopy. For example, a delivery device may be utilized, which may include a wire guide placed inside the tunnel. At least a portion of the support device 110 may then be advanced into the submucosal tunnel 38 with the guidance of the wire guide while visible under fluoroscopy. In other cases, the support device 110 may be deployed over the end of an endoscope. The support device 110 may comprise markers or indicators of another form to provide a medical professional with an indication of proper placement. When the submucosal tunnel 38 is formed with an injection procedure (as described above, the support device 110 may be configured such that it may be guided through gel or other injected fluid if that fluid remains in the submucosal tunnel during the deployment of the support device 110. In other embodiments, the deployment of the support device 110 may act to facilitate the flushing of the injected fluid out of the submucosal tunnel. Additional embodiments of a support device are described in detail below.

Figure 9:
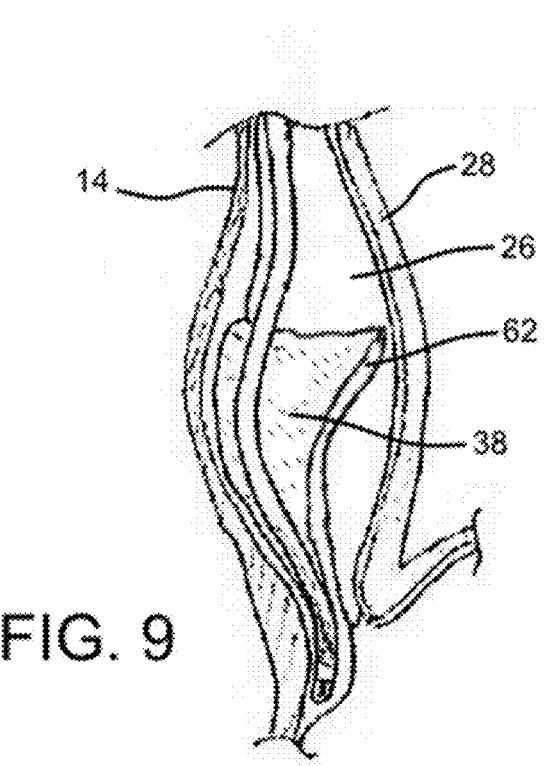
FIG. 9 is a sectional view of a submucosal tunnel formed near the distal end of the esophagus with a flap engaging the inner surface of the wall of the esophagus in accordance with the present disclosure.

Referring to FIG. 9, a seal at proximal end of the submucosal tunnel 38 may be formed by attaching or otherwise engaging a flap 62 of the submucosal tissue to the inner surface of the wall 28 of the native lumen 26. For example, as shown, the flap 62 may be attached to the wall 28 of the esophagus 14 such GI contents are prevented from traveling distally of flap 62 without entering the submucosal tunnel 38. Any suitable method of attaching the flap 62 to the wall 28 may be used.

Figure 10:
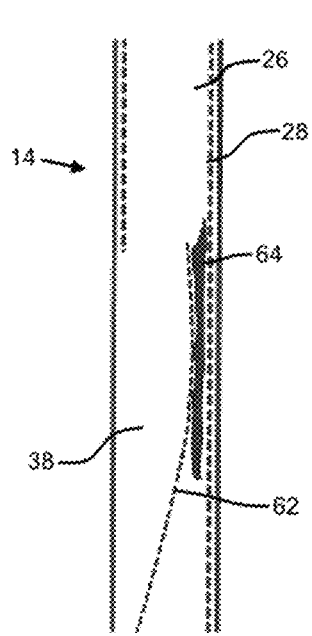
FIG. 10 is a side sectional view of a portion of an esophagus and a proximal portion of a submucosal tunnel, where an adhesive is used to maintain the submucosal tunnel in accordance with the present disclosure.

In some embodiments, as shown in FIG. 10, the flap 62 of submucosal tissue displaced from the submucosal layer 32 (see also FIG. 9) may be attached to the opposite-side wall 28 of the esophagus 14 via an adhesive 64. The adhesive 64 may be any suitable type of adhesive. For example and without limitation, the adhesive 64 may be a cyanoacrylate, a protein-based adhesive (i.e., mussel adhesive protein or a biomimetic), a UV curing adhesive, or a mucoadhesive (e.g., chitosan, carboxymethylcellulose, Carbomer). The adhesive 64 may be permanent, but in some embodiments it may be temporary (e.g., bioabsorbable). A temporary adhesive may be advantageous when it is only necessary to hold the flap 62 of the submucosal layer 32 in the depicted location during the installation of a gastrointestinal implant and/or during a period of tissue ingrowth. Other methods of attachment may be used in addition to or as an alternative to the adhesive 64. For example, it is contemplated that the flap 62 of the submucosal layer 32 may be attached to an opposite-side wall 28 by using tacks, by suturing, or by any other suitable attachment method.

Figure 11:
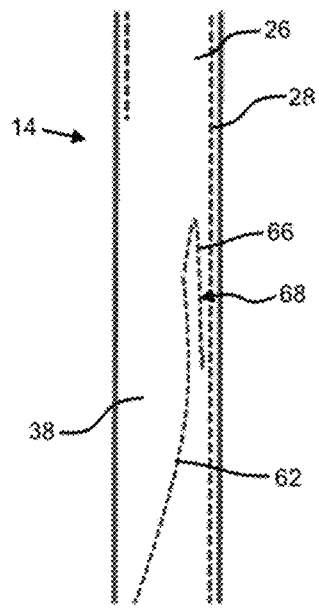
FIG. 11 is a side sectional view of a portion of an esophagus and a proximal portion of a submucosal tunnel in accordance with the present disclosure, where a flap of submucosal tissue is inverted in accordance with the present disclosure.

As depicted by FIG. 11, an end 66 of the flap 62 may be inverted or otherwise positioned such that the submucosal side 68 (e.g., the side natively facing away from the native lumen 26) faces and/or contacts the opposite-side wall 28 of the esophagus 14. This embodiment may be advantageous because submucosal tissue was found by the inventors to have a high degree of adhesion when compared to mucosal tissue, which is prone to necrose. It is contemplated that some of the mucosal tissue on the opposite-side wall 28 may be removed or otherwise damaged (e.g., intentionally damaged) to create an injury site such that the submucosal side 68 of the flap 62 contacts submucosal tissue and/or damaged mucosal tissue, which may further enhance the adhesion of the flap 62 to the opposite-side wall 28. Any other suitable technique may be used to enhance adhesion via tissue ingrowth or by another process or suitable technique (e.g., the associated tissue may be pre-treated with an RF current to create an injury site for accelerated tissue ingrowth).

Figure 12:
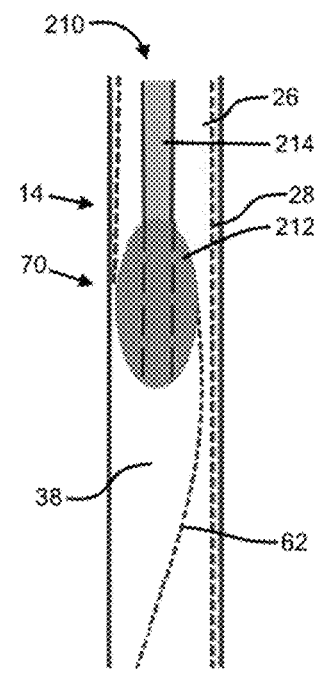
FIG. 12 is a side sectional view of a portion of an esophagus and a proximal portion of a submucosal tunnel, where a first embodiment of a support device is used to maintain the submucosal tunnel in accordance with the present disclosure.

One technique for facilitating attachment of the flap 62 to the opposite-side wall 28 is depicted by FIG. 12. As depicted, a support device 210, here including a balloon 212, may be positioned in the entrance 70 of the submucosal tunnel 38. The positioning of the support device 210 may occur after or during the tunneling process of FIG. 3, for example. Advantageously, the balloon 212 may provide a radial force directed outward such that flap 62 is pressed against the opposite-side wall 28, thereby holding the flap 62 in place, potentially under pressure, to facility adhesion (via tissue ingrowth or another method). While the balloon 212 may be inflated prior to its installation, it may be advantageous to maneuver the balloon 212 to the entrance 70 of the submucosal tunnel 38 while deflated (and relatively compact). The balloon 212 may then be inflated when at or near the entrance 70 of the submucosal tunnel 38.

The balloon 212 may be configured to be permanently placed at the entrance 70 of the submucosal tunnel 38, or it may be configured to be removed when adhesion between the flap 62 and the opposite-side wall 28 is sufficient. The period of time that the balloon 212 will be located within the gastrointestinal tract of the patient body may vary based on the time required for sufficient adhesion. In some instances, the balloon 212 may be inflated for only a few minutes (or shorter). In other instances (e.g., when tissue ingrown is used for adhesion), it may be necessary to leave the balloon 212 within the gastrointestinal tract for hours, days, weeks, or even longer.

When the medical procedure calls for the balloon 212 to remain in place for a significant period of time, it may be advantageous to provide a feeding tube 214 configured for the passage of GI contents therethrough. The feeding tube 214 may extend substantially through the balloon 212, may bypass the outer diameter of the balloon 212, or may otherwise be positioned such that the balloon 212 does not fully block the flow of GI contents through the gastrointestinal tract (or other passage through the body of the patient). In some embodiments, the feeding tube 214 may be a nasogastric or a percutaneous endoscopic gastrostomy (PEG) tube. The feeding tube 214 may extend proximally through the gastrointestinal tract to the mouth of a patient, but this is not required. The feeding tube 214, for example, may enter the gastrointestinal tract through an artificial opening created by a medical professional (e.g., in the esophagus).

Figure 13:
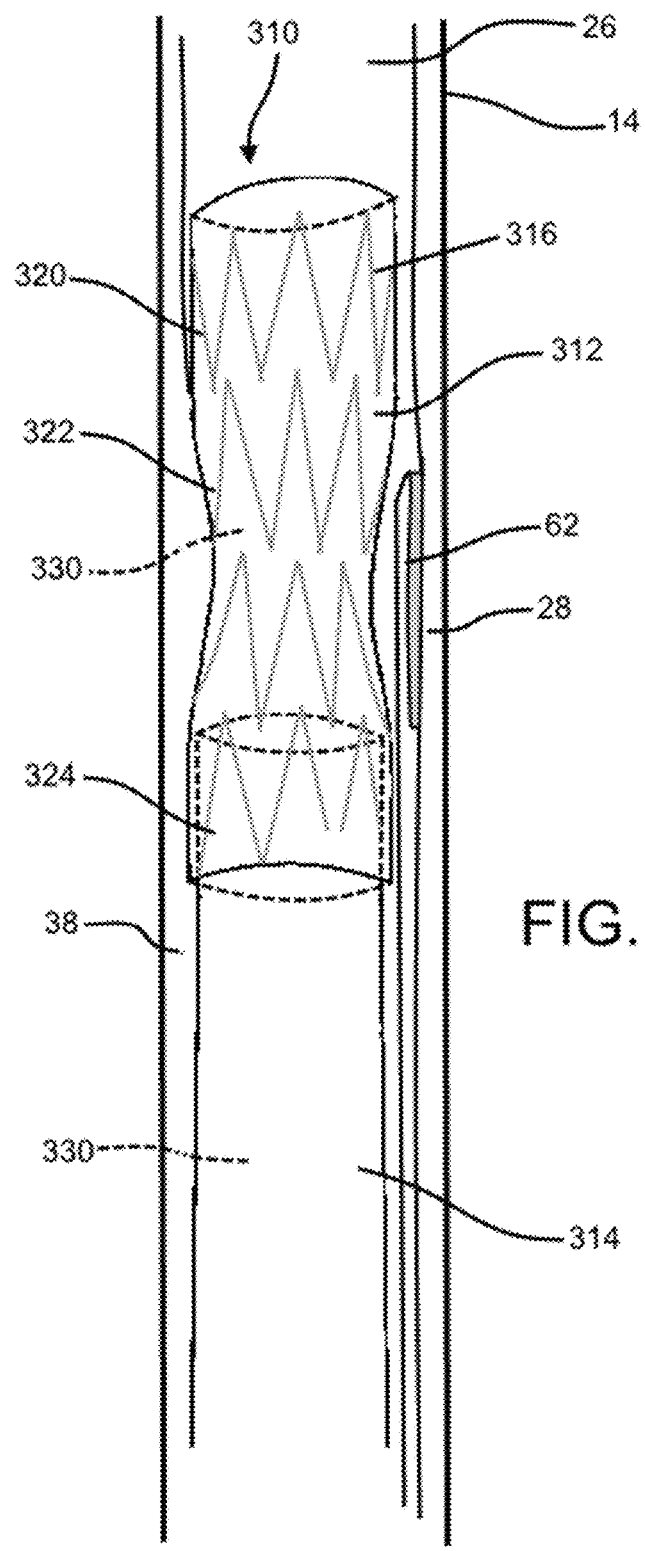
FIG. 13 is a side section view of a portion of the esophagus and a proximal portion of a submucosal tunnel, where a second embodiment of a support device is used to maintain the submucosal tunnel in accordance with the present disclosure.

FIG. 13 shows an embodiment of a support device 310. The support device 310 may be used as an alternative to the support device 210 described above with reference to FIG. 12, and it may be deployed to facilitate adhesion of the flap 62 to the opposite-side wall 28. Alternatively, the support device 310 could be deployed and installed after or during the removal of the support device 210. It is contemplated that the support device 210 (of FIG. 12) and the support device 310 (of FIG. 13) could be used together. For example, when the support device 310 includes an expandable stent (described in more detail below), the balloon 212 of the support device 210 may facilitate expansion of that stent.

The support device 310 of FIG. 13 may be a permanent gastrointestinal implant. Herein, a "permanent" implant is intended to remain in the body of a patient for a period longer than a period of time for installation, but not necessarily for the entirety of the patient's life. The support device 310 may include a support structure 312 and an artificial tunnel 314 (e.g., a hollow tube, a sleeve, or the like) extending distally from the support structure 312. While not shown, it is contemplated that a tube or other device could extend proximally from the support structure 312.

The support structure 312 may have a covered or uncovered stent 316 and a lumen 330 extending therethrough. The stent 316, which may be expandable, may be self-expanding or may expand under external pressures, for example from an inflatable balloon at the tip of a balloon catheter. The stent 316 may include any suitable stent pattern. One example of a stent pattern is the Z-stent or Gianturco stent design. The stent pattern may include a series of substantially straight segments or struts interconnected by a series of bent segments or bends. The bent segments may include acute bends or apices. The segments may be arranged in a zigzag configuration where the straight segments are set at angles relative to one another and are connected by the bent segments. The stent 316 may additionally or alternatively be formed of another stent pattern, such as an annular or helical stent pattern. Without limitation, the segments mentioned herein may be made from standard medical grade stainless steel or from nitinol or other shape-memory materials. The stent 316 is not required in all embodiments of the support structure 312, and the support structure 312 may additionally or alternatively include a balloon or other inflatable device, a substantially rigid or obstinate tube formed of a biocompatible material, of any other suitable device for providing support. It is contemplated that the support structure could be formed of bioabsorbable materials that dissolve over time.

The support structure 312 may be configured for being positioned at least partially within the native lumen 26 of the esophagus 14 and/or at least partially in the submucosal tunnel 38. For example, referring to the installed support structure 312 depicted in FIG. 13, the support structure 312 may have a first portion 320 positioned in the native lumen 26 of the esophagus 14. A second portion 322 of the support structure 312 may be positioned adjacent to the area where the flap 62 is adhered to the opposite-side wall 28, and a third portion 324 of the support structure 312 may be located in the submucosal tunnel 38.

The support structure 312 may have single or multiple cross-sectional dimensions (e.g., diameters) along its length. To illustrate (without limitation), the first portion 320 of the support structure 312 may have a relatively large diameter (e.g., from about 18-40 mm), the second portion 322 may have a relatively small diameter (e.g., from about 8-30 mm), and the third portion 324 may have a diameter similar to the diameter of the first portion 320. Advantageously, the first portion 320 having a relatively large diameter may be provide a relatively high radial force within the native lumen 26 of the esophagus 14 to prevent migration of the support structure 312. The second portion 322 having the relatively small diameter may be configured to provide a relatively low radial force at the entrance of the submucosal tunnel 38 to prevent pressure necrosis at that location and/or to prevent compromising the adhesion of the flap 62. The third portion 324 may be enlarged with respect to the second portion 322 and may be configured to receive the artificial tunnel 314, which may extend distally from the support structure 312. In some embodiments, the third portion 324 may provide a relatively high radial force on the submucosal tunnel 38, though this may not be required in all instances. Further, in some embodiments, the third portion 324 may have a diameter smaller than the diameter of the first portion 320 or otherwise provide less of an outward radial force than the first portion 320, which may be advantageous for to prevent compromising the submucosal tissue forming the submucosal tunnel 38.

While the support structure 312 is described herein as having a generally circular cross-section, the support structure 312 could alternatively have a cross-section of a different shape, and therefore where "diameter" is described herein, the description also applies to an alternative cross-sectional dimension. Further, it is contemplated that the outward radial force provided by the support structure 312 may vary even where the diameter does not vary (e.g., a spring constant or other mechanical characteristic provided by the first portion 320—of the support structure 312 may be higher than a second spring constant provided at the second portion 322 and/or third portion 324 of the support structure 312). While only three different diameters are described herein, it is contemplated that the support structure 312 could have more than, or less than, three diameters along its length. In some embodiments, the support structure 312 may have a diameter that continuously changes along its length.

The support structure 312 may be positioned differently with respect to the description depicted in FIG. 13. For example, in FIG. 14, the support structure 312 is located entirely in the native lumen 26 of the esophagus 14. Advantageously, this may provide a greater area of contact between the support structure 312 and the native walls of the esophagus 14, which may enhance the anti-migration features of the support structure 312 without increasing its length. It is contemplated that the support structure 312 may have a substantially constant outer diameter when it is configured to be entirely located within the native lumen 26. It also is contemplated that the support structure 312 may be located primarily, or even entirely, in the submucosal tunnel 38. An additional anti-migration feature for the support structure may be included, and may include the use of a bulking agent within the wall 28 of the native lumen 26. The bulking agent may provide a ridge or shelf for maintaining the positioning of the support structure 312.

The artificial tunnel 314 may extend through at least a portion of the submucosal tunnel 38. A proximal end 326 of the artificial tunnel 314 may be attached to the distal end 328 of the support structure 312. In the depicted embodiment, the outer diameter of the proximal end 326 of the artificial tunnel 314 is configured to fit within the inner diameter of the distal end 328 such that the proximal end 326 of the artificial tunnel 314 is substantially immovable relative to the distal end 328 of the support structure 312. This fit may be a friction fit to ensure a suitable attachment, but an adhesive or another form of attachment may additionally or alternatively be used. In other embodiments, proximal end 326 of the artificial tunnel 314 may fit around the outer diameter of the support structure 312. The present disclosure is not limited to embodiments where the support structure 312 fits around the outer diameter of the artificial tunnel 314 (or vice versa), and other suitable types of attachment may be used. Further, it is contemplated that another object may be placed between the proximal end 326 of the artificial tunnel 314 and the distal end 328 of the support structure 312.

The artificial tunnel 314 may be a compliant and/or flexible member (at least with respect to the support structure 312) with a lumen 330 extending therethrough from the proximal end 326 to a distal end (not shown). The artificial tunnel 314 may be primarily made of an elastomer (e.g., silicone, polyurethane), a non-woven polymer (e.g., ePTFE, Tyvek, electrospun polymers), a woven or knitted polymer (e.g., Dacron), or any other suitable material. In some embodiments, the artificial tunnel 314 may incorporate a stent. The lumen 330 of the artificial tunnel 314 may be configured for passage of GI contents therethrough. For example, it is contemplated that the walls of the lumen 330 may be lubricated or otherwise configured for suitable friction with passing GI contents.

While the artificial tunnel 314 may be permeable, semi-permeable, or non-permeable, it may be advantageous for the artificial tunnel 314 to be semi-permeable. The semi-permeability may facilitate tissue ingrowth while still substantially preventing GI contents from leaking out of the lumen 330 of the lumen 330. Similarly, the artificial tunnel 314 could be non-permeable and could have an external texture or other external surface characteristic configured to allow and facilitate tissue ingrowth. Additionally or alternatively, the artificial tunnel 314 may be attached to the submucosal tunnel 38 with an adhesive, with mechanical tacks, by suturing, or by any other suitable attachment method. In some embodiments, the artificial tunnel 314 may remain movable (e.g., unattached) with respect to at least a portion of the submucosal tunnel 38.

The artificial tunnel 314 may include a support structure (e.g., a stent or other suitable structure) with a compliant covering forming its walls. When the artificial tunnel 314 has a support structure, the support structure may be included along the entirety of the length of the artificial tunnel 314, or it may be located in select locations where support is needed, but not in locations where compliance and flexibility is advantageous. The artificial tunnel 314 may additionally or alternatively have an anti-torsion feature that prevents the artificial tunnel 314 from twisting. The artificial tunnel 314 may be installed with the support structure 312 or separately from the support structure 312. In some embodiments, the artificial tunnel 314 may be attached to the support structure 312 at the installation site in the gastrointestinal tract. Like the support structure 312, the artificial tunnel 314 may be formed of bioabsorbable materials. In some embodiments, the support structure 312 and the artificial tunnel 314 may be a single, integral, one-piece component.

Figure 14:
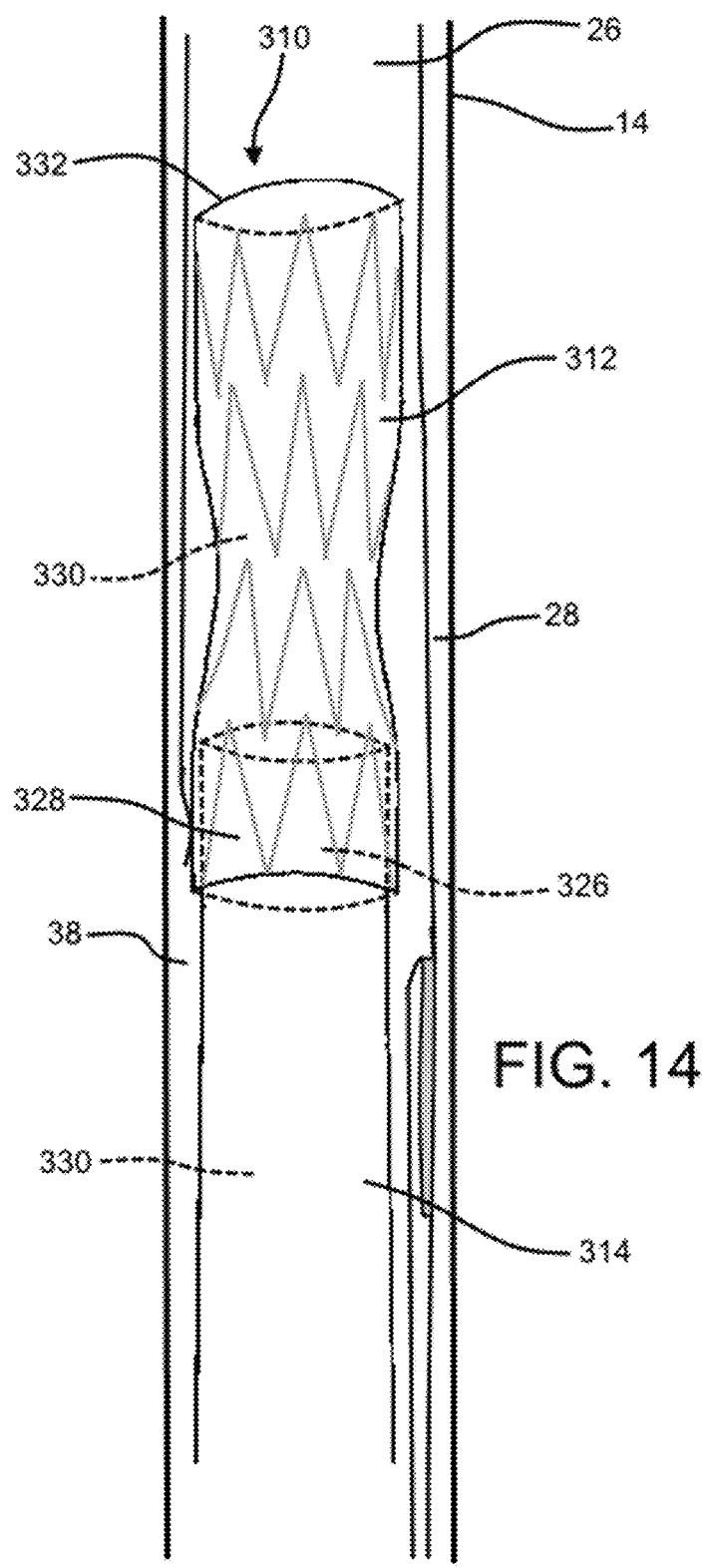
FIG. 14 shows the second embodiment of the support device of FIG. 8, where a support structure of the support device is located within a native lumen of an esophagus in accordance with the present disclosure.

Referring to FIG. 14, a mouth 232 (which may also be referred to as a "proximal opening" herein) of the support structure 312 may be configured to direct GI contents into the submucosal tunnel 38. The mouth 232 of the support structure 312 preferably contacts entirety of the wall 28 of the native lumen 26 of the esophagus 14 such that GI contents cannot bypass the mouth 232. Sequentially, GI contents moving distally through the gastrointestinal tract will pass from the native lumen 26 of the esophagus 14 and through the mouth 232, which directs the GI contents into the portion of the lumen 330 within the support structure 312. As the GI contents move further distally, they will then enter the submucosal tunnel 38 (here by way of the portion of the lumen 330 within the artificial tunnel 314). Advantageously, the GI contents may move through the submucosal tunnel 38 and bypass at least a portion of the natural gastrointestinal tract. It is contemplated that the support structure 312 could operate without the artificial tunnel 314 (particularly where a portion of the support structure 312 is located within the submucosal tunnel 38), but the artificial tunnel 314 may be advantageous for maintaining the submucosal tunnel 38 by providing support and/or by preventing the submucosal tunnel 38 from growing shut.

The above figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

We claim:

1. A support device for a gastrointestinal implant, the support device comprising:
   a lumen configured to extend through a submucosal tunnel;
   a mouth located at a proximal end of the lumen and in fluid communication with the lumen, wherein the mouth is configured to face proximally within a gastrointestinal tract to receive GI contents, and wherein the mouth is configured to direct the GI contents into the lumen;
   a support structure, wherein the lumen extends through the support structure, and wherein the support structure is configured to apply an outward radial force on an inner wall of the gastrointestinal tract; and
   an artificial tunnel extending distally from the support structure and forming at least a portion of the lumen, wherein the artificial tunnel is configured to extend through the submucosal tunnel.

2. The support device according to claim 1, wherein the support structure includes a first portion and a second portion located distally of the first portion, and wherein a diameter of the first portion is larger than a diameter of the second portion.

3. The support device according to claim 2, wherein the first portion is configured to be located within a native lumen of the gastrointestinal tract, and wherein the second portion is configured to be located in a submucosal tunnel.

4. The support device according to claim 1, wherein the artificial tunnel is semi-permeable.

5. The support device according to claim 1, wherein the artificial tunnel includes an outer surface with a surface characteristic configured to facilitate tissue ingrowth.

6. The support device according to claim 1, further comprising:
   a feeding tube including the lumen and the mouth; and
   a balloon including the support structure;
   wherein the feeding tube extends substantially through the balloon.

7. The support device according to claim 1, wherein the support structure is configured to apply a pressure to a flap of submucosal tissue placed in contact with an opposite-side wall of the gastrointestinal tract.

8. A method for providing a submucosal tunnel, the method comprising:
   forming the submucosal tunnel within an inner wall of a native lumen of a gastrointestinal tract; and
   deploying a support device configured to maintain the submucosal tunnel, the support device including a support structure, a lumen extending through the support structure, and a mouth located at a proximal end of the lumen and in fluid communication with the lumen, wherein deploying the support device includes locating at least a portion of the lumen within the submucosal tunnel.

9. The method of claim 8, wherein deploying the support device includes locating at least a portion of the support structure proximally of the submucosal tunnel such that the support structure applies an outward radial force on an inner wall of the native lumen of the gastrointestinal tract.

10. The method of claim 8, wherein deploying the support structure includes maneuvering the support structure through the gastrointestinal tract in a collapsed state and then expanding the support structure to an expanded state such that the support structure contacts the inner wall of the native lumen.

11. The method of claim 8, wherein the support device includes an artificial tunnel extending distally from the support structure and forming at least a portion of the lumen, and wherein deploying the support device includes locating the artificial tunnel such that it extends through at least a portion of the submucosal tunnel.

12. The method of claim 11, wherein the artificial tunnel includes a distal mouth configured to discharge GI contents into a native portion of the gastrointestinal tract.

13. The method of claim 8, wherein forming the submucosal tunnel includes displacing a flap of submucosal tissue from a wall of the native lumen of the gastrointestinal tract and adhering the flap to the opposite-side wall of the native lumen.

14. The method of claim 13, wherein forming the submucosal tunnel further includes forming an injury site on the opposite-side wall of the native lumen and placing the flap in contact with the injury site.

15. A method for forming a bypass of a portion of a gastrointestinal tract, the method comprising:
   injecting a fluid beneath a first layer to separate the first layer from a second layer, thereby forming a fluid-filled pocket;
   forming a first incision at a proximal end portion of the fluid-filled pocket; and
   forming a second incision in a distal end portion of the fluid-filled pocket,
   wherein the first incision, second incision, and pocket define a tunnel.

16. The method of claim 15, wherein the fluid is injected at a plurality of locations.

17. The method of claim 15, the method further comprising deploying a reinforcement device within the tunnel.

18. The method of claim 17, the method further comprising expanding the reinforcement device within the tunnel.

19. The method of claim 15, wherein the first incision is located in an esophagus of a patient, and wherein the second incision is located in a stomach of a patient.

20. The method of claim 15, wherein the pocket extends from an esophagus of a patient and bypasses at least a portion of a stomach of the patient.

* * * * *